(12) United States Patent
Hara

(10) Patent No.: US 8,152,299 B2
(45) Date of Patent: Apr. 10, 2012

(54) FUNDUS CAMERA

(75) Inventor: Hiroshi Hara, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 114 days.

(21) Appl. No.: 12/831,182

(22) Filed: Jul. 6, 2010

(65) Prior Publication Data

US 2011/0007273 A1     Jan. 13, 2011

(30) Foreign Application Priority Data

Jul. 10, 2009   (JP) ................................ 2009-163899

(51) Int. Cl.
- *A61B 3/14* (2006.01)
- *A61B 3/10* (2006.01)
- *G03B 29/00* (2006.01)

(52) U.S. Cl. ........... 351/206; 351/214; 351/221; 396/18

(58) Field of Classification Search .................. 351/206, 351/214, 221; 396/18
See application file for complete search history.

(56) References Cited

U.S. PATENT DOCUMENTS 7,848,625 B2 * 12/2010 Mizuno et al. .................. 396/18

2004/0075813 A1   4/2004   Mizukusa
2007/0183760 A1   8/2007   Mizuno

FOREIGN PATENT DOCUMENTS

| JP | 2003-0024279 A | 1/2003 |
|---|---|---|
| JP | 2007-0209433 A | 8/2007 |

* cited by examiner

*Primary Examiner* — Jack Dinh

(74) *Attorney, Agent, or Firm* — Canon U.S.A., Inc., IP Division

(57) ABSTRACT

A fundus camera includes an illumination optical system, an observation photographic optical system, a photographic diaphragm unit located in a position conjugate with the subject's eye in the observation photographic optical system, and an imaging unit disposed in the observation photographic optical system. The photographic diaphragm unit includes a first photographic diaphragm fixed during capturing of a still image and a second photographic diaphragm movable during capturing of a moving image. The fundus camera further includes a diaphragm driving unit configured to move the second photographic diaphragm on a plane orthogonal to an optical axis, an image recording unit configured to capture, with the first photographic diaphragm, a still image based on an output of the imaging unit and, with the second photographic diaphragm, a moving image based on an output of the imaging unit, and a display unit configured to display an image captured by the imaging unit.

11 Claims, 8 Drawing Sheets

FUNDUS CAMERA

BACKGROUND OF THE INVENTION

1. Field of the Invention

The present invention relates to a fundus camera which captures a fundus image of a subject's eye.

2. Description of the Related Art

As a method for capturing a fundus image, there is a fluorescent photographing method which inspects a running condition of a blood vessel of a subject's eye by using a fluorescent agent. In fluorescent photographing, a ruptured or difficult blood flowing portion of the vessel can be identified by checking a change of a blood flow on the fundus image of the subject's eye in real time. The change of the blood flow can be checked more minutely by stereoscopically capturing the fundus image. In typical stereoscopic capturing of the fundus image, a fundus camera body is slightly moved left and right, and two fundus images different from each other in parallax are captured. The two fundus images are arrayed left and right to be stereoscopically observed by naked eyes or polarized glasses.

However, the method based on stereoscopic observation by the naked eyes requires some skill, and hence the fundus images may not be satisfactorily observed in many cases. The method using the polarized glasses has a problem that a structure of an apparatus is complex.

In order to move the fundus camera body left and right to capture the two fundus images, the fundus images must be aligned to perform photographing twice. As compared with typical still image capturing of a posterior part of the fundus, the processing takes more time and labor Japanese Patent Application Laid-Open No. 2003-024279 discusses a fundus camera which can stereoscopically observe fundus images by continuously displaying a plurality of images at predetermined time intervals, the fundus images having been captured by moving a camera body left and right.

Japanese Patent Application Laid-Open No. 2007-209433 discusses a fundus camera which can acquire two images having parallaxes without moving a fundus camera body by continuously performing a plurality of photographing operations by one shutter button operation and moving the position of a photographic diaphragm for each photographing operation.

However, in the case of the fundus camera discussed in Japanese Patent Application Laid-Open No. 2003-024279, the fundus camera body must be moved left and right to perform photographing, and the captured images must be stored first to be reproduced. Thus, real-time checking cannot be performed.

In the case of the fundus camera discussed in Japanese Patent Application Laid-Open No. 2007-209433, only a predetermined number of fundus images can be acquired within a predetermined period of time. Acquisition of fundus images and stereoscopic observation cannot be performed at any arbitrary timing.

In the above fundus camera, the fundus camera body or the photographic diaphragm is moved only left and right to capture images. Thus, no parallax information can be acquired nor any stereoscopic observation can be performed for horizontally-aligned vessels.

SUMMARY OF THE INVENTION

The present invention is directed to a fundus camera which enables stereoscopic observation of an uneven structure on a fundus.

According to an aspect of the present invention, a fundus camera includes an illumination optical system configured to illuminate a subject's eye with excitation light of a predetermined wavelength, an observation photographic optical system configured to observe and photograph fluorescent light reflected from a fundus of the subject's eye with the excitation light, a photographic diaphragm unit located in a position conjugate with the subject's eye in the observation photographic optical system, the photographic diaphragm unit including a first photographic diaphragm that is fixed during capturing of a still image and a second photographic diaphragm that is movable during capturing of a moving image, an imaging unit disposed in the observation photographic optical system, a diaphragm driving unit configured to move the second photographic diaphragm on a plane orthogonal to an optical axis, an image recording unit configured to capture, by using the first photographic diaphragm, a still image based on an output of the imaging unit and to capture, by using the second photographic diaphragm, a moving image based on an output of the imaging unit, and a display unit configured to display an image captured by the imaging unit.

According to the fundus camera of exemplary embodiment of the present invention, for example, even for a blood vessel horizontally running on the fundus, an image having a parallax can be acquired, and stereoscopic observation can be performed.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
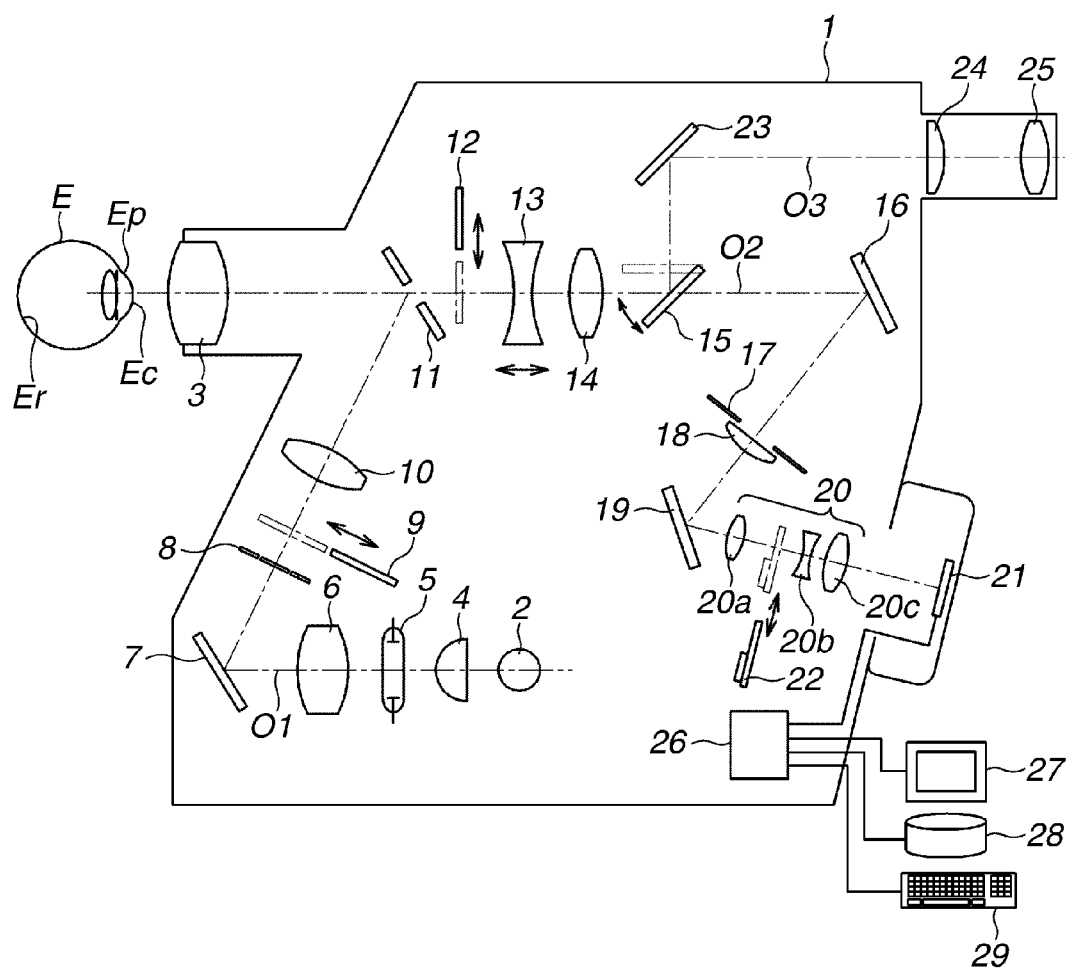
FIG. 1 illustrates a configuration of a fundus camera according to an exemplary embodiment of the present invention.

FIG. 1 illustrates a configuration of a fundus camera according to a first exemplary embodiment of the present invention. In a casing 1 of the fundus camera, there is provided an illumination optical system, which includes components from an observation light source 2 to an objective lens 3 disposed corresponding to a subject's eye E. On its optical path O1, there are arrayed a condenser lens 4, a photographic light source 5, a relay lens 6, a mirror 7, a diaphragm 8 having a ring-shaped opening, an excitation filter 9 that is able to be freely inserted into/pulled out of the optical path to transmit only excitation light of a predetermined wavelength, a relay lens 10, and a perforated mirror 11. A halogen lamp for emitting stationary light is used for the observation light source 2, and a flash light source is used for the photographic light source 5.

An observation photographic optical system is provided behind the perforated mirror 11. On its optical path O2, there are sequentially arrayed a barrier filter 12, a focusing lens 13, a photographic lens 14, a movable mirror 15, a mirror 16, a fundus mask diaphragm 17, a field lens 18, and a mirror 19. In a reflection direction of the mirror 19, an image-forming lens group 20 including lenses 20a to 20c and an imaging plane of a digital camera 21, which is an imaging unit, are arrayed. A photographic diaphragm unit 22, which is freely movable on the optical path O2, is disposed between the lens 20a and the lens 20b of the image-forming lens group 20 located in a position optically conjugate with a pupil of the subject's eye E.

On an optical path O3 of a finder optical system in a reflection direction of the movable mirror 15, there are arrayed a mirror 23, a field lens 24, and an eyepiece lens 25.

An output of the digital camera 21 is connected to a control unit 26. A monitor 27, which is a display unit, disposed outside the casing 1, an image storage memory 28, which is an image recording unit, and a keyboard 29 are connected to the control unit 26. The keyboard 29 is used for selecting and inputting setting relating to an operation of the fundus camera, such as an amount of light to be applied to the subject's eye E, and operating displaying of a fundus image stored in the image storage memory 28 on the monitor 27.

By effects of the excitation filter 9 and the barrier filter 12, the fundus camera of the present exemplary embodiment can capture fluorescent light generated by excitation light projected onto a fundus Er of the subject's eye E. A fluorescent image of the fundus is observed and captured by inserting the excitation filter 9 and the barrier filter 12 into the optical path. By moving the filters out of the optical path, a fundus image can be observed and captured by visible reflected light.

A driving motor for the movable mirror 15, the excitation filter 9, and the barrier filter 12, and a photographing switch are connected to the control unit 26 via a control line (not illustrated). The digital camera 21 is operated under control of the control unit 26.

Under the control of the control unit 26, the digital camera 21 is controlled for capturing a fundus image, and outputs a captured image to the monitor 27 and the image storage memory 28 via the control unit 26.

Figure 2:
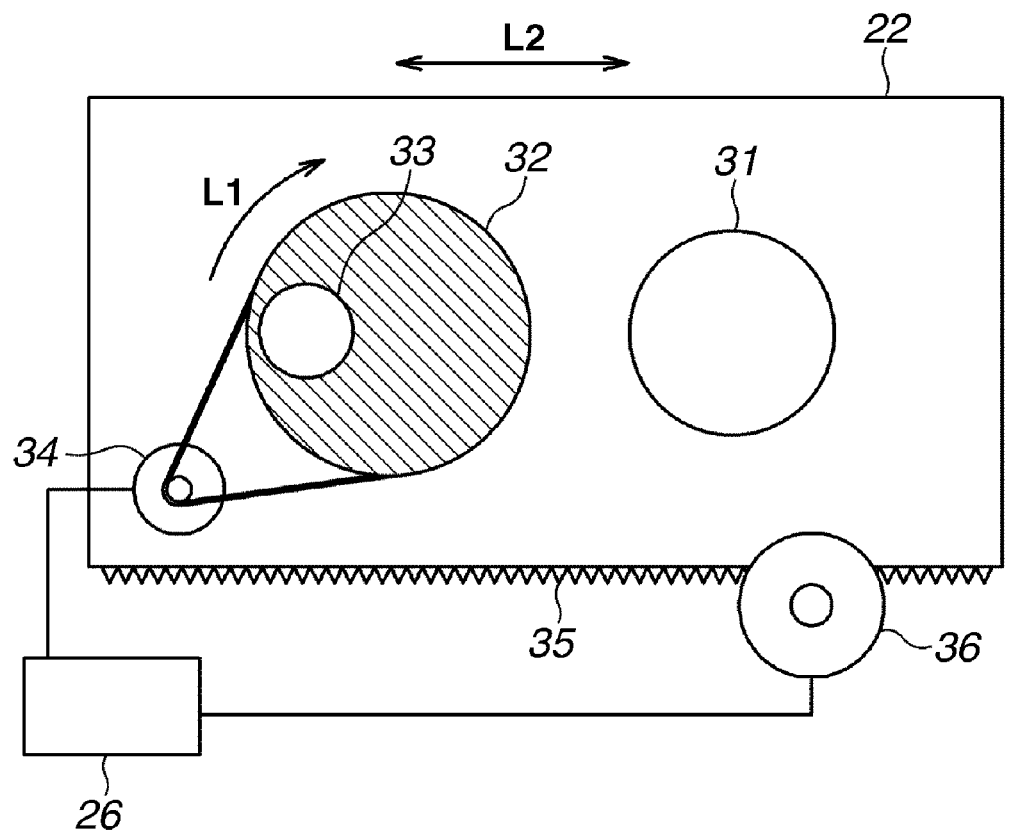
FIG. 2 illustrates a photographic diaphragm unit of the fundus camera.

FIG. 2 illustrates a configuration of the photographic diaphragm unit 22. The photographic diaphragm unit 22 includes a photographic diaphragm 31 for still image capturing, which is a first photographic diaphragm and fixed during capturing, and a photographic diaphragm 32 for moving image capturing, which is a second photographic diaphragm and movable during capturing. A diaphragm hole 33 is bored in the photographic diaphragm 32. The photographic diaphragm 32 is configured to be rotated around an optical axis by a motor 34. The entire photographic diaphragm unit 22 is connected to a motor 36 via a gear 35, and the motors 34 and 36 are connected to the control unit 26.

The photographic diaphragm 32 can be moved in a rotational direction of an arrow L1 by driving the motor 34, and reciprocated on a plane orthogonal to the optical axis. The photographic diaphragm unit 22 can be moved in a horizontal direction of an arrow L2 via the gear 35, and switched between the photographic diaphragm 31 for still image capturing and the photographic diaphragm 32 for moving image capturing by driving the motor 36.

A diameter of the photographic diaphragm 31 is larger than that of the diaphragm hole 33 of the photographic diaphragm 32 for moving image capturing. During still image capturing, a range wider than that of one moving image capturing operation can be photographed. A diameter of the photographic diaphragm 32 is larger than that of the photographic diaphragm 31. A photographing range when the photographic diaphragm 32 makes one rotation in the rotational direction of the arrow L1 is wider than that during still image capturing using the photographic diaphragm 31.

Figure 3:
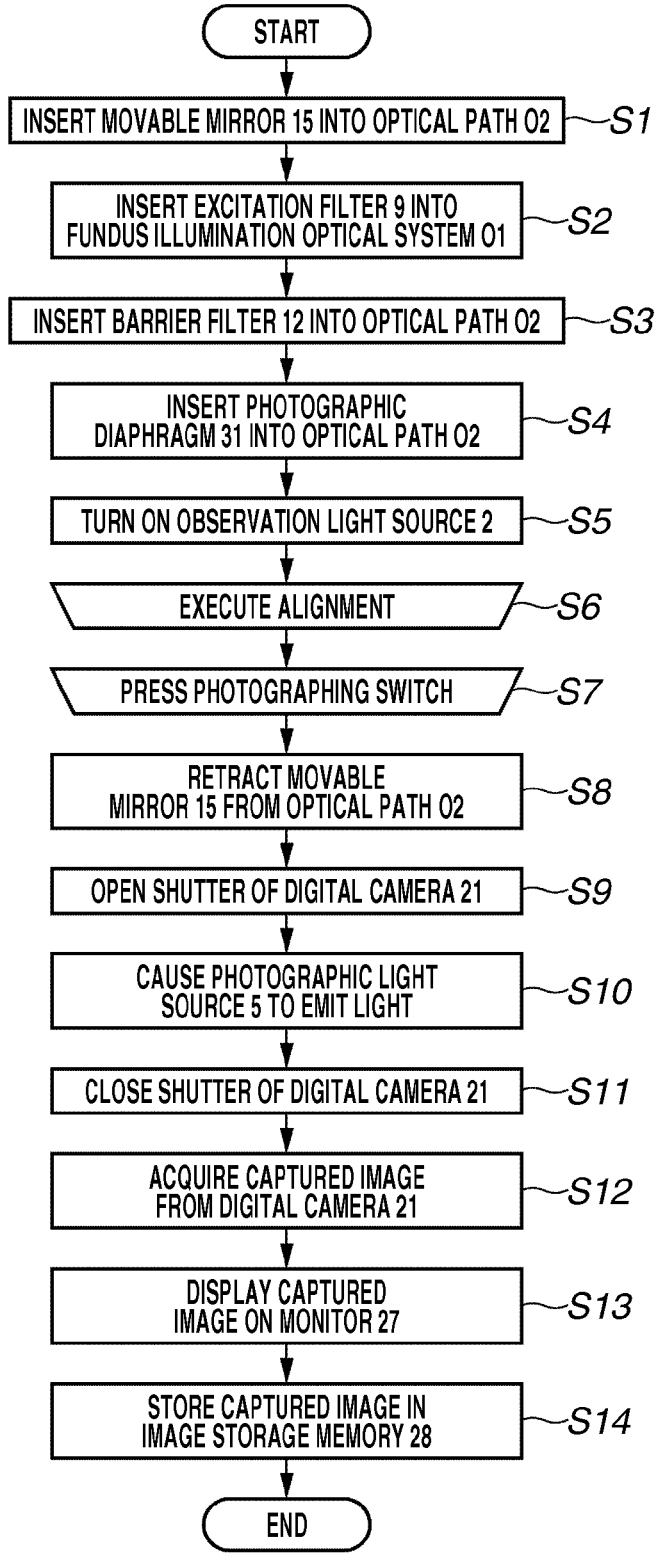
FIG. 3 is a flowchart illustrating an operation of capturing a still fundus fluorescent image.

FIG. 3 is a flowchart illustrating an operation when a still fundus fluorescent image is captured. When a photographing operation is started, in step S1, the control unit 26 inserts the movable mirror 15 into the optical path O2. By this operation, the fundus image is passed through the optical path O3 of the finder optical system to be displayed on the eyepiece lens 25. In step S2, the control unit 26 inserts the excitation filter 9 into the illumination optical system O1. In step S3, the control unit 26 inserts the barrier filter 12 into the optical path O2. In step S4, the control unit 26 inserts the photographic diaphragm 31 for still image capturing included in the photographic diaphragm unit 22 into the optical path O2. By this operation, the still fundus fluorescent image can be observed and captured. In step S5, the control unit 26 turns ON the observation light source 2.

A light flux emitted from the observation light source 2 is passed through the condenser lens 4, the photographic light source 5, and the relay lens 6 to be reflected on the mirror 7. The light reflected on the mirror 7 is passed through the diaphragm 8, the excitation filter 9, and the relay lens 10 to be reflected around the perforated mirror 11, and passed through the pupil Ep of the subject's eye E to illuminate the fundus Er. The fundus image reflected on the fundus Er is passed through the objective lens 3 and the perforated mirror 11 of the optical path O2, and through the barrier filter 12, the focusing lens 13, and the photographic lens 14, and reflected on the movable mirror 15 to reach the optical path O3. On the optical path O3, the fundus image is reflected on the mirror 23, and observed by an operator via the field lens 24 and the eyepiece lens 25.

In step S6, the operator performs alignment while observing the fundus image displayed on the eyepiece lens 25 of the optical path O3 of the finder optical system after the passage through the above optical paths. After the alignment, the processing proceeds to step S7, and the operator presses a photographing switch (not illustrated).

After the pressing of the photographing switch in step S7, then in step S8, the control unit 26 retracts the movable mirror 15 from the optical path O2. In step S9, the control unit 26 opens a shutter of the digital camera 21. In step S10, the control unit 26 causes the photographic light source 5 to emit light.

In step S11, the control unit 26 closes the shutter of the digital camera 21. In step S12, the control unit 26 acquires a captured image from the digital camera 21. In step S13, the control unit 26 displays the captured image acquired in step S12 on the monitor 27. In step S14, the control unit 26 stores the captured image in the image storage memory 28 to terminate the processing.

Figure 4:
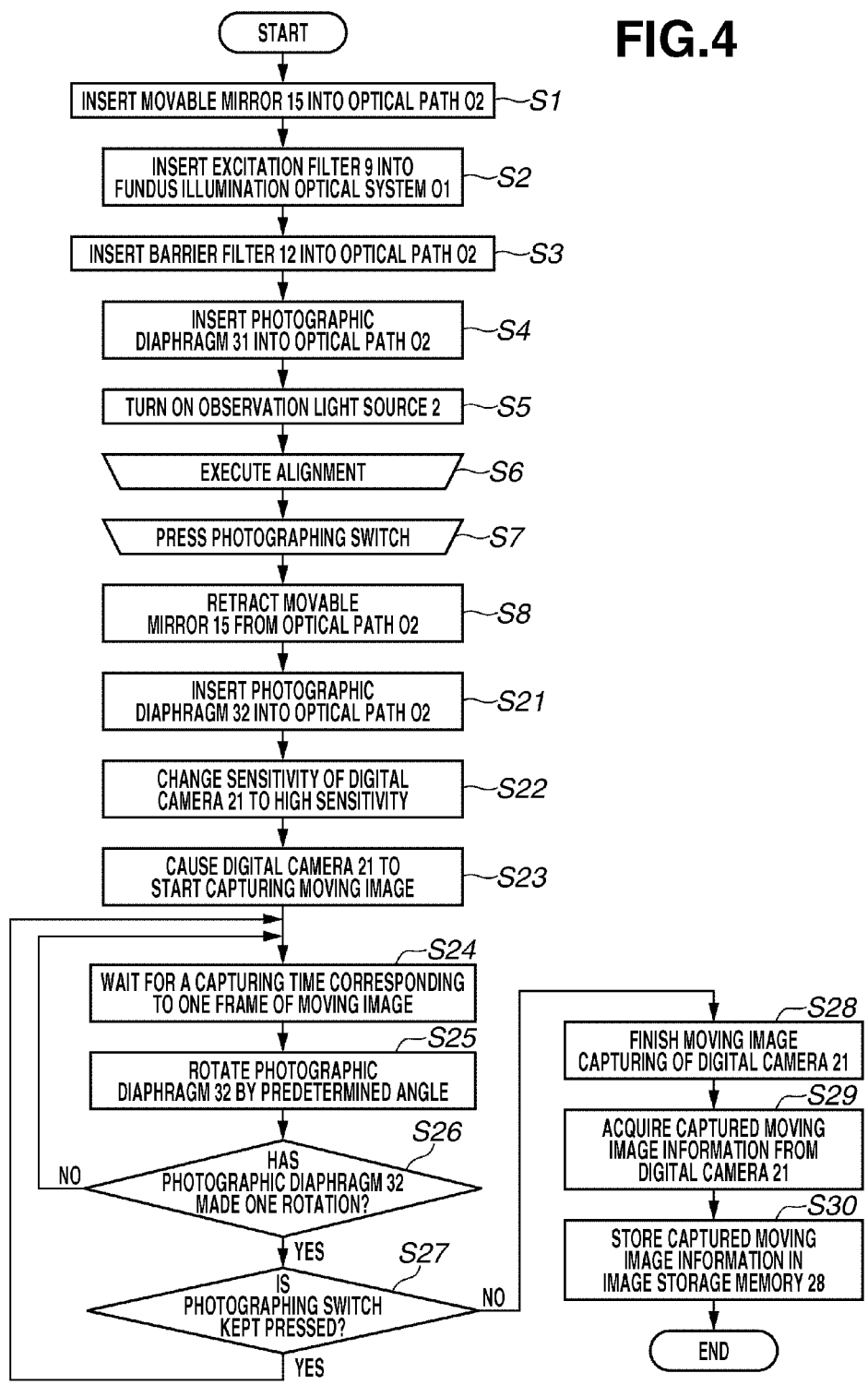
FIG. 4 is a flowchart illustrating an operation of capturing a moving fundus fluorescent image.

FIG. 4 is a flowchart illustrating an operation when a moving fundus fluorescent image is captured. The operation is similar to that of the still fundus fluorescent image capturing in steps S1 to S8, and thus the description of this portion is omitted.

After the alignment performed up to step S8, then in step S21, the control unit 26 inserts the photographic diaphragm 32 for moving image capturing included in the photographic diaphragm unit 22 into the optical path O2 by driving the motor 36. By this operation, the control unit 26 can retract the photographic diaphragm 31 for still image capturing from the optical path O2 to capture a moving image. In step S22, the control unit 26 changes sensitivity of the digital camera 21 to high sensitivity so that the fundus fluorescent image can be captured with the observation light source 2. In step S23, the control unit 26 causes the digital camera 21 to start capturing a moving image.

In step S24, the control unit 26 waits for a capturing time corresponding to one frame of the moving image. This waiting time is 1/30 seconds when the moving image frame rate is 30 frames per second. In step S25, the control unit 26 rotates the photographic diaphragm 32 at a predetermined angle by driving the motor 34. A rotational angle per frame is 12 degrees, for example, when the moving image frame rate is 30 frames per second and the photographic diaphragm 32 makes one rotation per second.

Figure 5:
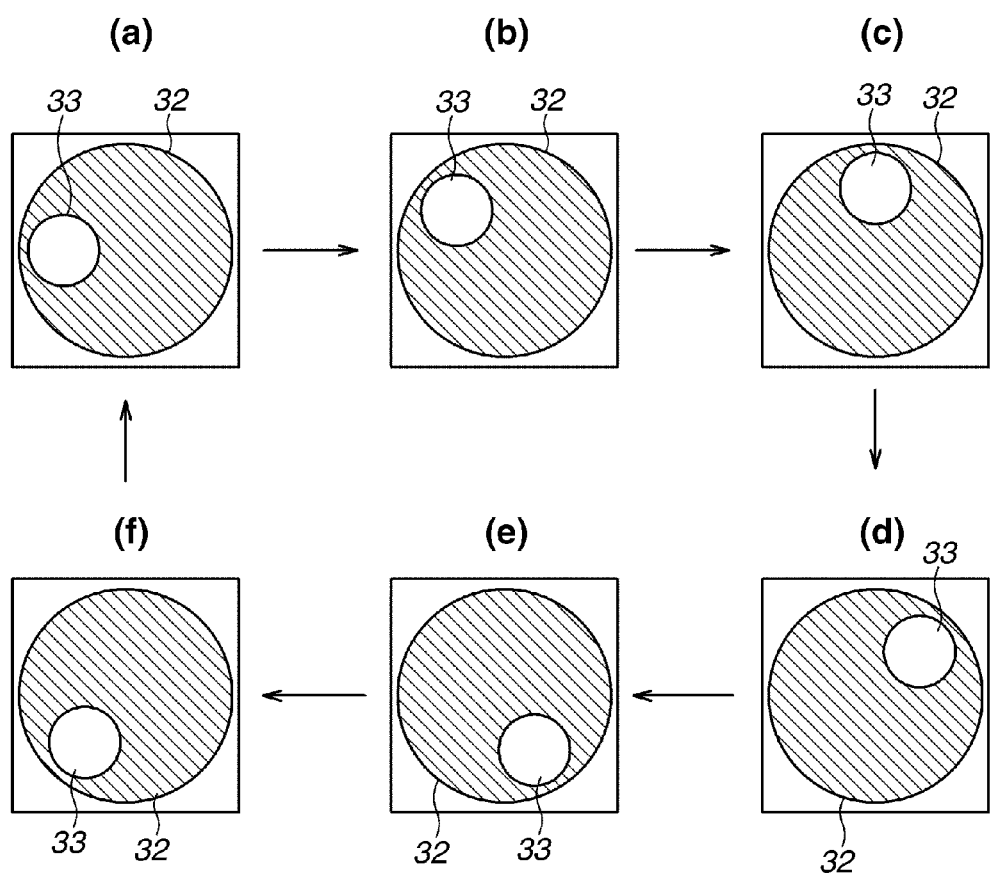
FIG. 5 illustrates diaphragm hole positions when a photographic diaphragm is rotated.

By rotating the photographic diaphragm 32, as illustrated in FIG. 5, the diaphragm hole 33 rotates from a position (a) up to a position (f). After one rotation of the photographic diaphragm 32, the diaphragm hole 33 returns to the position (a).

In step S26, the control unit 26 determines whether the photographic diaphragm 32 has made one rotation. If the control unit 26 determines that the photographic diaphragm 32 has not yet made one rotation (NO in step S26), the processing returns to step S24. If the control unit 26 determines that the photographic diaphragm 32 has made one rotation (YES instep S26), the processing proceeds to step S27. In step S27, the control unit 26 determines whether the photographing switch is kept pressed. If the photographing switch is determined to be kept pressed (YES in step S27), the processing returns to step S24. If the photographing switch is determined not to be kept pressed (NO in step S27), the processing proceeds to step S28. In step S28, the control unit 26 finishes the stereoscopic moving image capturing of the digital camera 21.

In step S29, the control unit 26 acquires information of the captured moving image from the digital camera 21. In step S30, the control unit 26 stores the captured moving image in the image storage memory 28, and terminates the processing.

Figure 6:
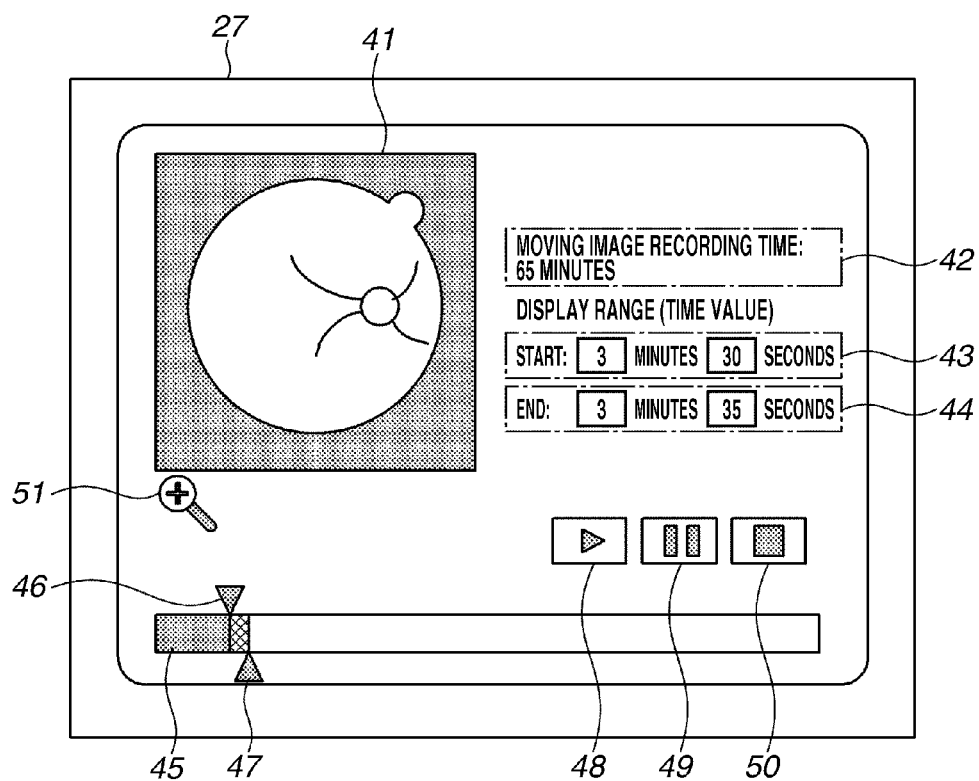
FIG. 6 illustrates a monitor screen.

FIG. 6 illustrates a screen of the monitor 27 when the stereoscopic moving fundus fluorescent image is selected from the image storage memory 28 to be displayed. The monitor 27 shows an image display section 41 for displaying the stereoscopic moving fundus fluorescent image and a display section 42 for displaying a recording time of the stereoscopic moving fundus fluorescent image.

The monitor 27 includes a start time input section 43 for setting a moving image playback time, and an end time input section 44. On the screen lower portion of the monitor 27, a time display axis 45 indicating time axes for setting start time and end time is displayed. On the time display axis 45, an arrow 46 indicating start time and an arrow 47 indicating end time are displayed. The monitor 27 further displays a playback button 48 for playing back and controlling the moving image, a pause button 49, and a stop button 50. The monitor 27 displays an enlargement button 51 for enlarging and displaying a part of the image displayed in the image display section 41.

In order to set time for starting moving image playback, start time is roughly designated by inputting a numeral to an input area of the start time input section 43 via the keyboard or a method for sliding the arrow 46 on the time display axis 45. In order to set time for stopping moving image playback, as in the case of the start time setting, end time is roughly designated by inputting a numeral to the end time input section 44 by using the keyboard or a method for sliding the arrow 47 on the time display axis 45. Designated values of the start time and the end time are adjusted and set by a movement cycle unit of the photographic diaphragm 32 of a period of one rotation of the photographic diaphragm 32. By associating the playback button 48, the pause button 49, and the stop button 50 with specific keys of the keyboard, playing-back of the moving image can be controlled based on an input from the keyboard.

In the state illustrated in FIG. 6, inputting of a key corresponding to the playback button 48 enables repeated playing-back of a set specific range of the stereoscopic moving fundus fluorescent image.

In the fundus camera, by performing moving image capturing while rotating the diaphragm hole 33 of the photographic diaphragm 32 around the optical axis, an image resulting from photographing the fundus Er from a plurality of angles including horizontal and vertical angles is acquired, enabling stereoscopic observation of an uneven structure on the fundus Er. Thus, even an uneven image having a parallax other than a horizontal direction can be stereoscopically observed, and a horizontal blood vessel of the image unobtainable in the case of an image of only a horizontal direction can be stereoscopically observed.

The enlargement button 51 is for enlarging and displaying the image displayed in the image display section 41. By associating the enlargement button 51 with a specific key of the keyboard, the displayed image can be enlarged based on an input from the keyboard. By permitting movement within a display range of the image corresponding to a specific key of the keyboard, a specific area of the image can be enlarged and displayed, enabling more minute observation.

Thus, when the diaphragm hole 33 is rotated in the arrow direction L1 of FIG. 2, a moving image having a viewpoint moved in the rotational direction can be acquired. By associatively driving the motors 34 and 36 to reciprocate the diaphragm hole 33 in the horizontal direction, a moving image having a viewpoint mainly moved in the horizontal direction can be acquired.

The photographic diaphragm 32 is moved in the rotational direction as illustrated in FIG. 5. However, for the purpose of simplifying the configuration of the apparatus, the diaphragm hole 33 maybe reciprocated only in the horizontal direction L2 by driving the motor 36 without using the motor 34.

In the first exemplary embodiment, the moving fundus fluorescent image is played back by the frame rate equal to that during the capturing. However, by changing the frame rate during the playing-back, a stereoscopic image can be acquired more easily or each frame can be observer more minutely.

Figure 7:
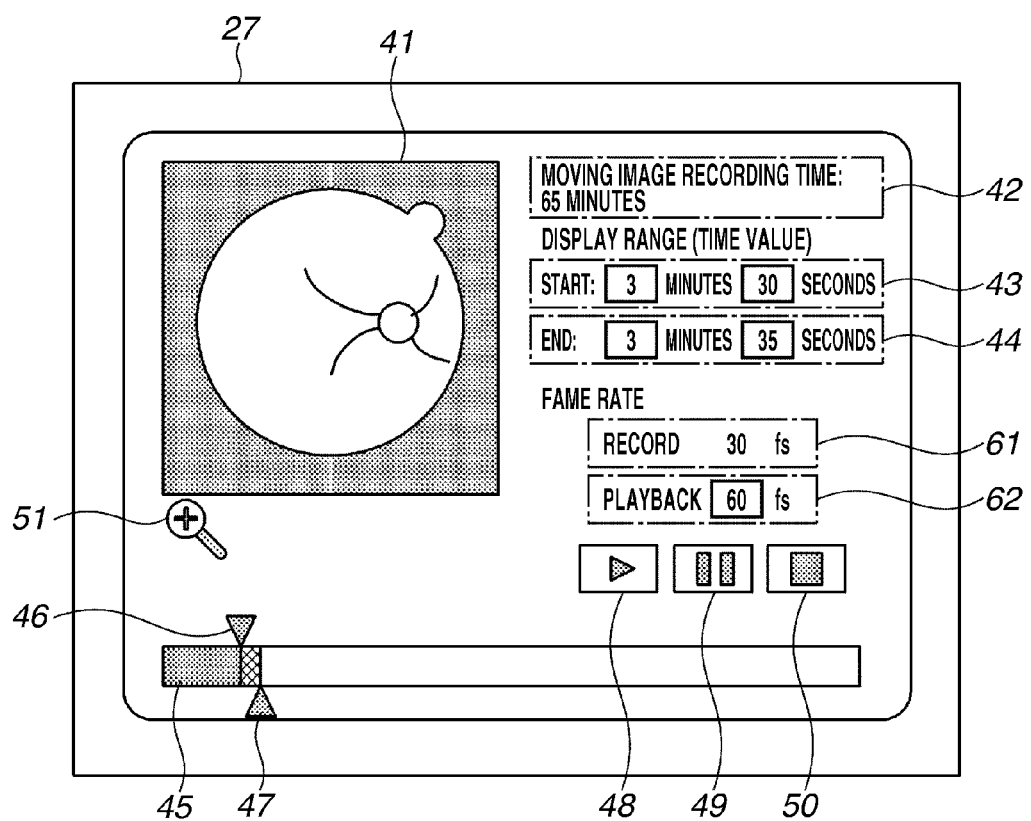
FIG. 7 illustrates a monitor screen.

FIG. 7 illustrates a screen of a monitor 27 configured so that a frame rate during playing-back of a moving fundus fluorescent image can be changed to a value different from that during capturing. Portions having functions similar to those of FIG. 6 are denoted by similar reference numerals.

In a second exemplary embodiment of the present invention, the monitor 27 includes a display section 61 for displaying a frame rate during moving image capturing, and an input section 62 for inputting and setting a frame rate during moving image playing-back. An observer inputs a frame rate during moving image playing-back to the input section 62 by using a keyboard 29 while the moving image playing-back is stopped, and can display the image at the input frame rate by starting the moving image playing-back.

In the first and second exemplary embodiments, the captured moving fundus fluorescent image is directly displayed on the monitor 27. However, parallaxes of pixels of respective images can be calculated with a plurality of frames of a moving image set as a group to generate a range image. Then, the range image can be displayed on the monitor 27.

The generation of the range image is performed, when an image having the diaphragm hole 33 moved in the rotational direction L1 of FIG. 2 by driving the motor 33 is captured, by calculating and acquiring three-dimensional coordinate data via a well-known method based on a pair of images of a position where the diaphragm hole 33 is opposite by 180 degrees to the optical axis.

Figure 8:
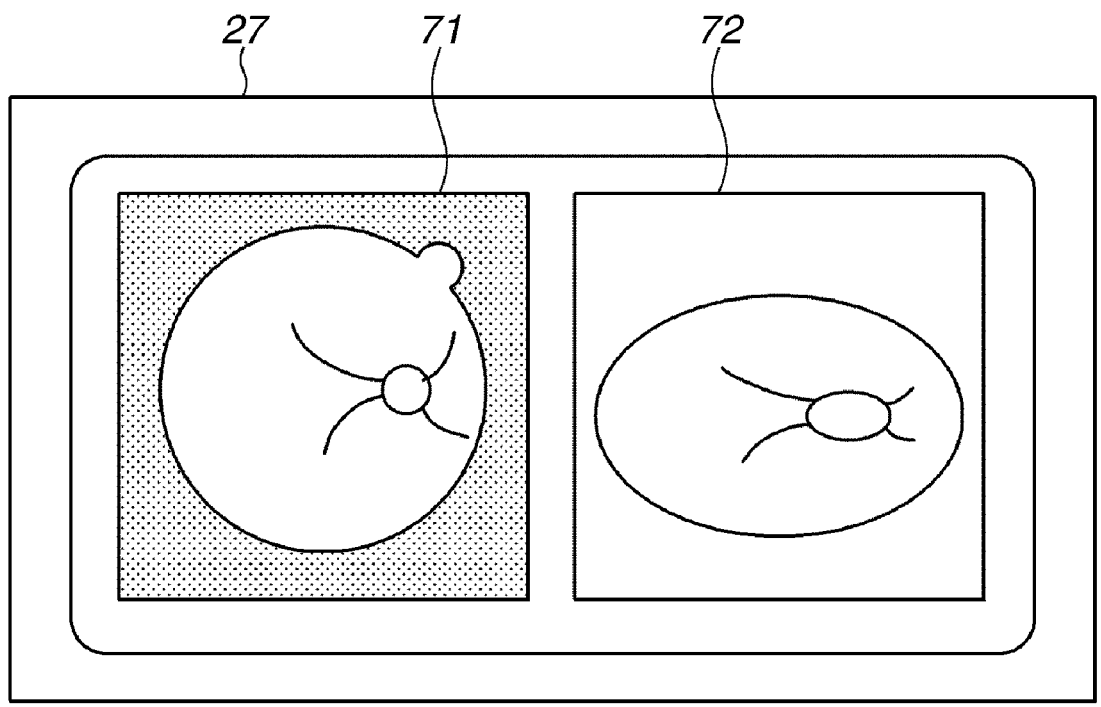
FIG. 8 illustrates a monitor screen.

FIG. 8 illustrates a screen of a monitor 27 according to a third exemplary embodiment of the present invention, displaying a perspective view of a three-dimensional image based on a generated range image. A display section 71 on the left half of the monitor 27 displays a representative image of images used for range image generation. For the representative image, an image of a smallest frame number among the images used for the range image generation is used. A display section 72 on the right half of the monitor 27 displays a three-dimensional fundus image acquired from the generated range image.

At least two sets of images changed in angles can be used. By a pair of images obtained by combining images of 180-degree diagonal positions among these images, based on a result of an image processing unit for acquiring a plurality of range images, a more accurate three-dimensional image can be generated.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-163899 filed Jul. 10, 2009, which is hereby incorporated by reference herein in its entirety.

What is claimed is:

1. A fundus camera comprising:
an illumination optical system configured to illuminate a subject's eye with excitation light of a predetermined wavelength;
an observation photographic optical system configured to observe and photograph fluorescent light reflected from a fundus of the subject's eye with the excitation light;
a photographic diaphragm unit located in a position conjugate with the subject's eye in the observation photographic optical system, the photographic diaphragm unit including a first photographic diaphragm that is fixed during capturing of a still image and a second photographic diaphragm that is movable during capturing of a moving image;
an imaging unit disposed in the observation photographic optical system;
a diaphragm driving unit configured to move the second photographic diaphragm on a plane orthogonal to an optical axis;
an image recording unit configured to capture, by using the first photographic diaphragm, a still image based on an output of the imaging unit and to capture, by using the second photographic diaphragm, a moving image based on an output of the imaging unit; and
a display unit configured to display an image captured by the imaging unit.

2. The fundus camera according to claim 1, wherein the display unit repeatedly reproduces a specific range of the captured moving image.

3. The fundus camera according to claim 2, wherein the specific range of the captured moving image is a movement cycle unit of the second photographic diaphragm.

4. The fundus camera according to claim 1, wherein the display unit is configured to enlarge and display a part of the captured image.

5. The fundus camera according to claim 1, wherein a diameter of the second photographic diaphragm is smaller than a diameter of the first photographic diaphragm.

6. The fundus camera according to claim 1, wherein a range of moving image capturing is narrower than a range of still image capturing.

7. The fundus camera according to claim 1, wherein the imaging unit is driven with sensitivity higher during moving image capturing than during still image capturing.

8. The fundus camera according to claim 1, wherein the diaphragm driving unit applies rotational motion around the optical axis to the second photographic diaphragm.

9. The fundus camera according to claim 8, further comprising an image processing unit configured to calculate, based on at least two pairs of images acquired from a diagonal position of the diaphragm moved by the diaphragm driving unit, parallaxes of respective pixels to generate a range image.

10. The fundus camera according to claim 9, wherein the display unit is configured to stereoscopically display an image of the fundus based on a processing result by the image processing unit.

11. The fundus camera according to claim 1, wherein the display unit is configured to change a frame rate of the captured moving image to be displayed.

* * * * *